US00PP12213P2

(12) United States Plant Patent
Zimmermann

(10) Patent No.: US PP12,213 P2
(45) Date of Patent: Nov. 20, 2001

(54) HOP PLANT NAMED 'YCR ACCESSION NO. 14'

(75) Inventor: Charles E. Zimmermann, Prosser, WA (US)

(73) Assignee: Yakima Chief Ranches, Inc., Sunnyside, WA (US)

( * ) Notice: Subject to any disclaimer, the term of this patent is extended or adjusted under 35 U.S.C. 154(b) by 0 days.

(21) Appl. No.: 09/287,403

(22) Filed: Apr. 6, 1999

(51) Int. Cl.[7] ..... A01H 5/00

(52) U.S. Cl. ..... Plt./236

(58) Field of Search ..... Plt./236

*Primary Examiner*—Anne Marie Grünberg
(74) *Attorney, Agent, or Firm*—Stratton Ballew PLLC

(57) ABSTRACT

A new hop plant variety is disclosed. The new variety is used for its bittering and aromatic properties. The new variety is moderately tolerant to powdery mildew and Sphaerotheca. The new variety produces a medium size compact cone with good pickability and storageability. The cones mature early, and yield a crop of 2650 to 2880 pounds per acre (2970 to 3230 kg/ha).

6 Drawing Sheets

BACKGROUND AND SUMMARY OF INVENTION

This invention relates to a new and distinct variety of hop plant, and more particularly to a new hop plant variety of unknown parentage which was discovered among plants created as part of a controlled breeding program. The new variety has been stably reproduced over successive generations. Discovery of the new variety and initial reproduction by root cuttings was carried out in a research nursery in Prosser, Wash., U.S.A. Subsequent asexual reproduction took place in Granger, Wash., U.S.A.

THE DRAWINGS

DESCRIPTION OF THE VARIETY

Figure 1:
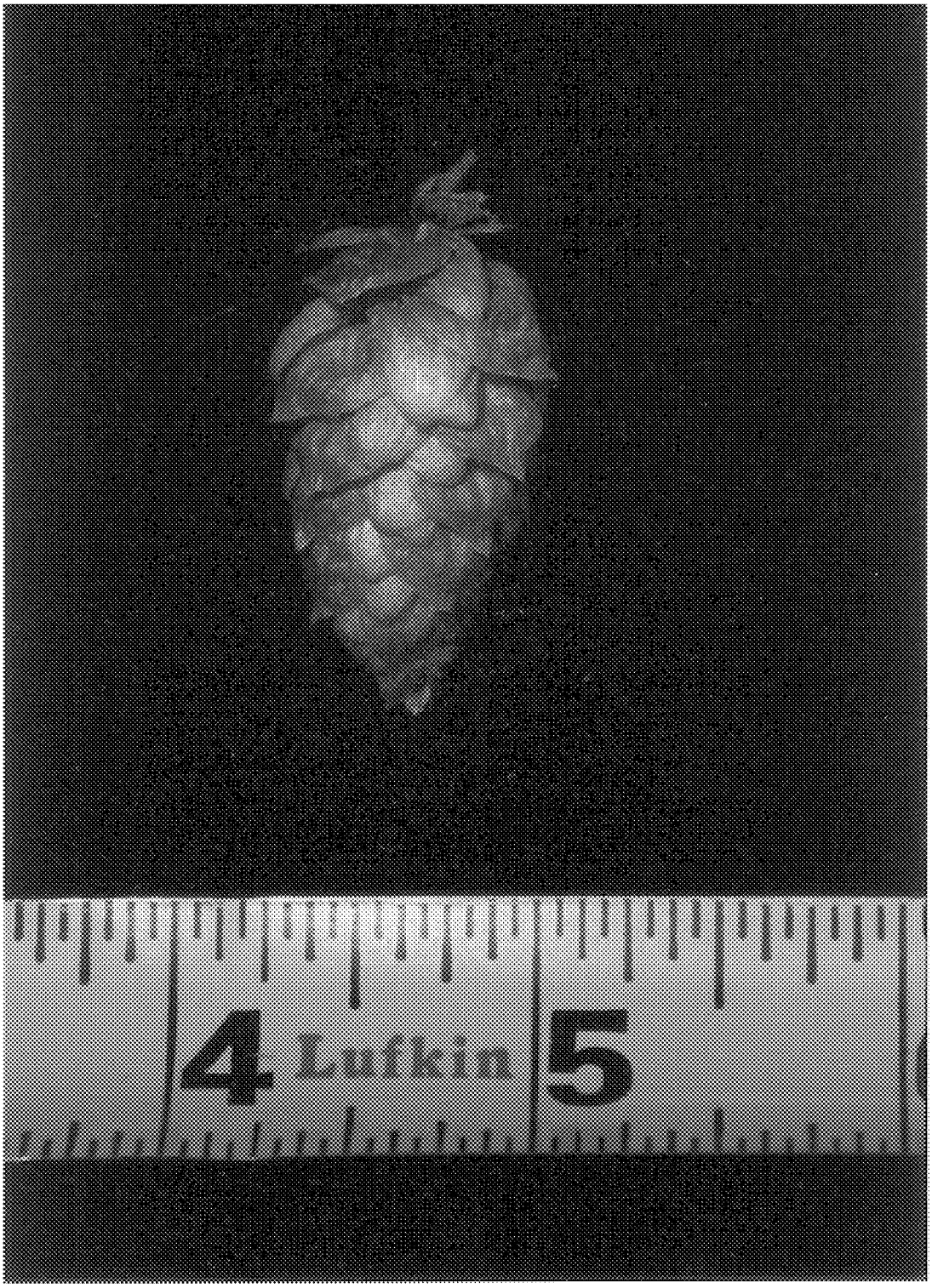
FIG. 1 shows a hop cone of the new hop plant variety.
Figure 2:
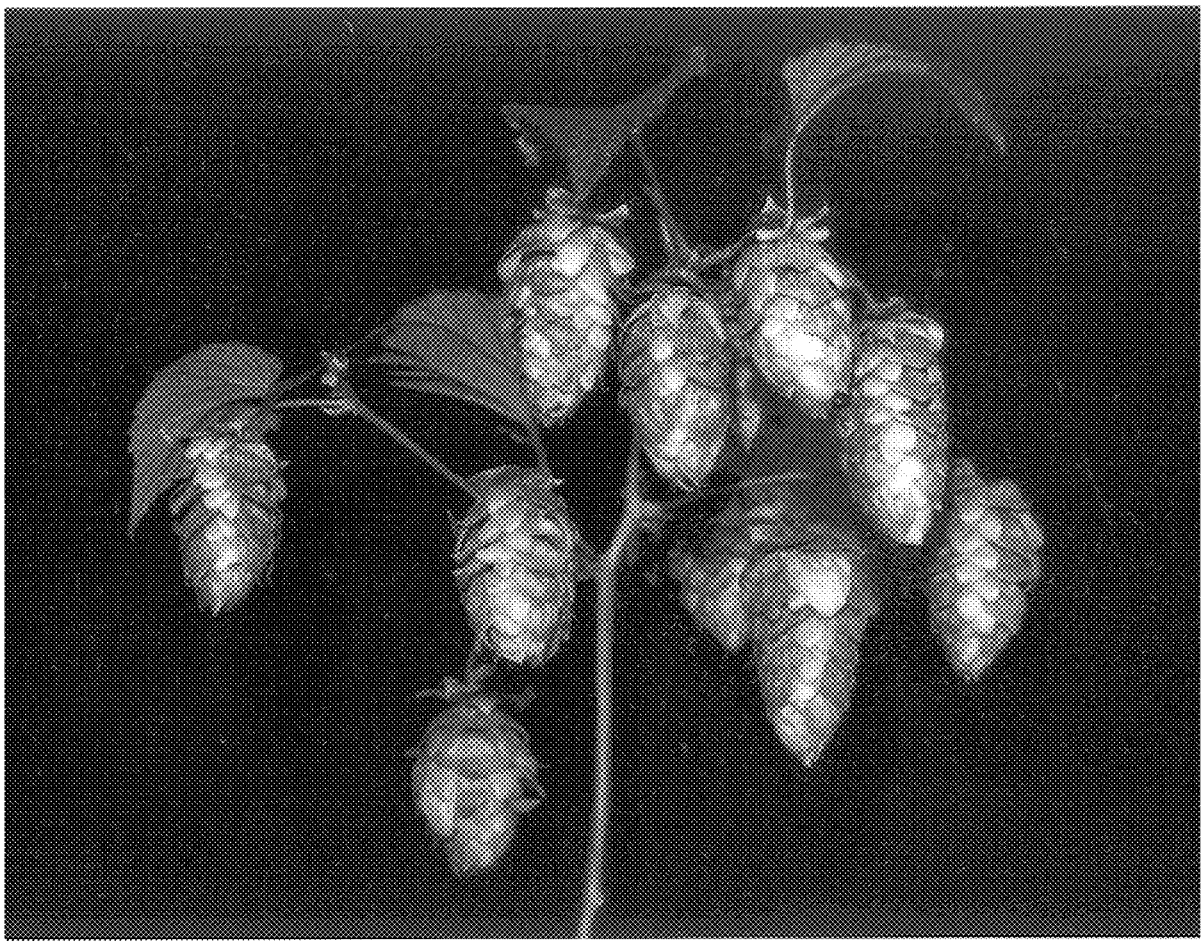
FIG. 2 shows a cluster of hop cones of the new hop variety.
Figure 3:
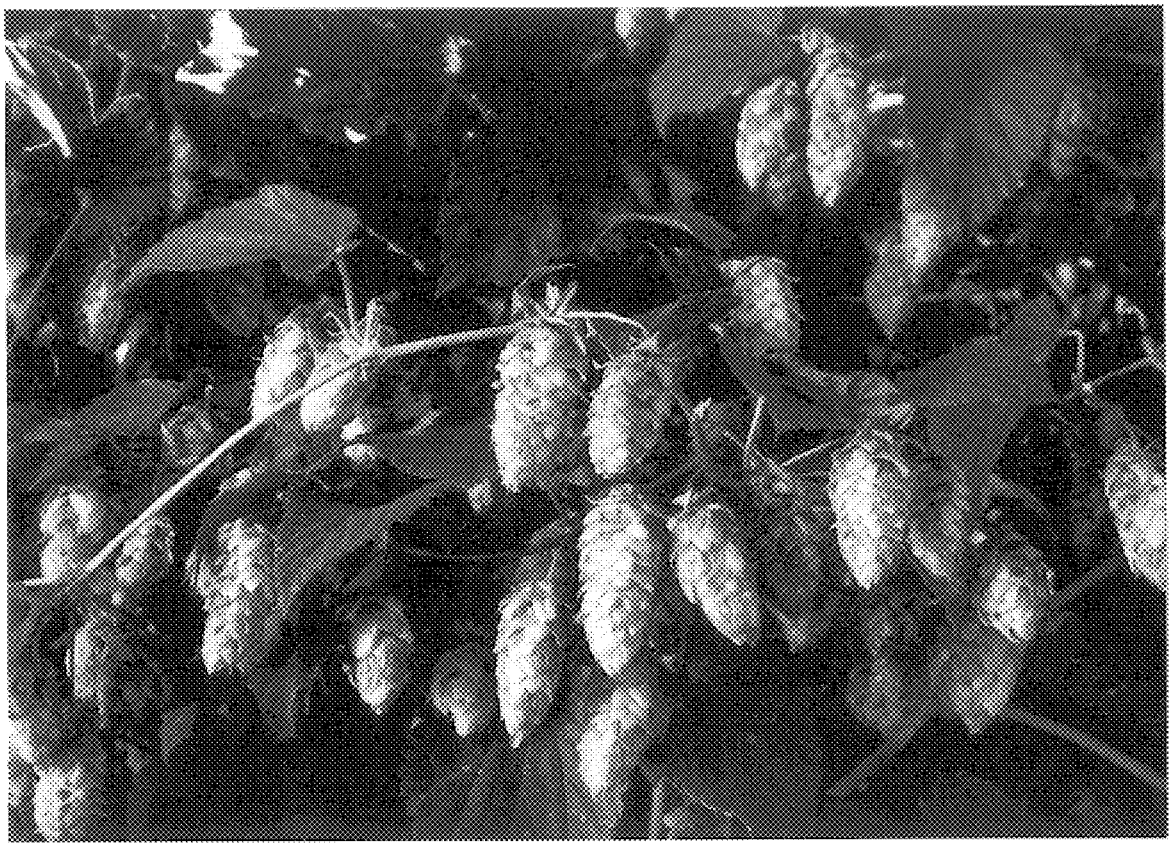
FIG. 3 shows a cluster of hop cones of the new hop variety.
Figure 4:
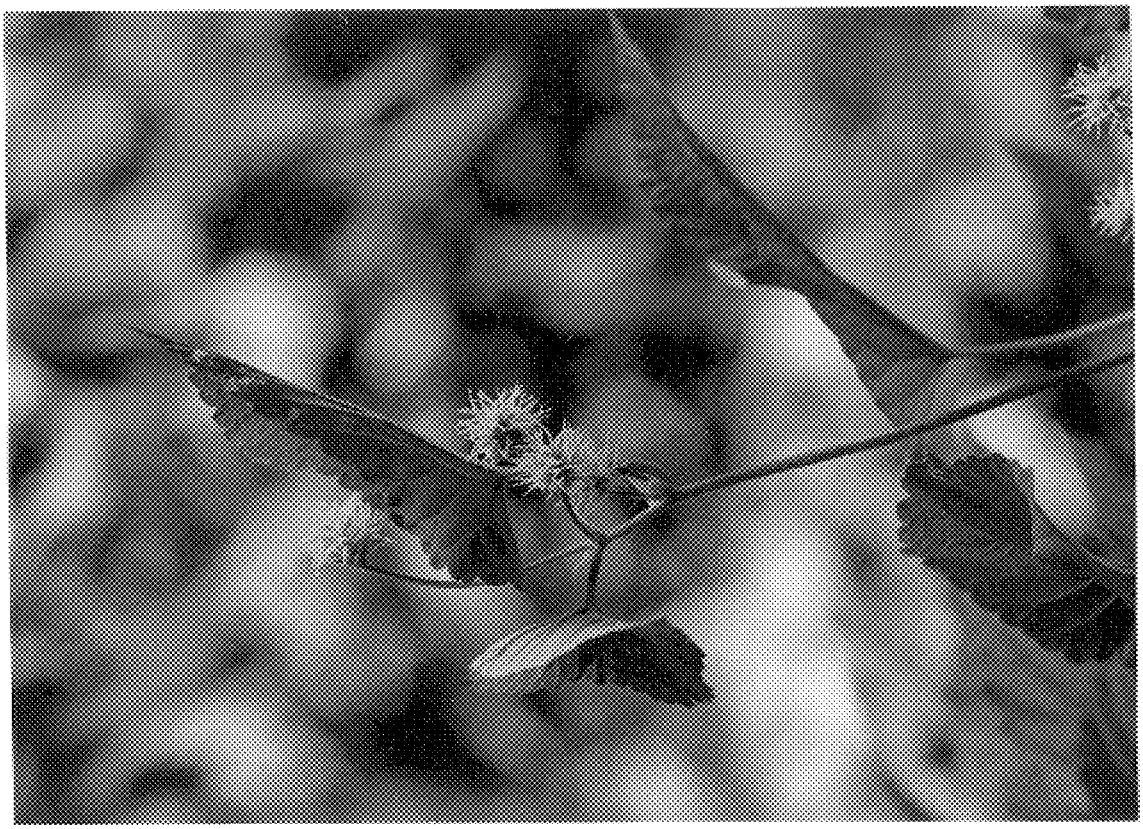
FIG. 4 shows a blossom and leaf of the new hop plant variety.
Figure 5:
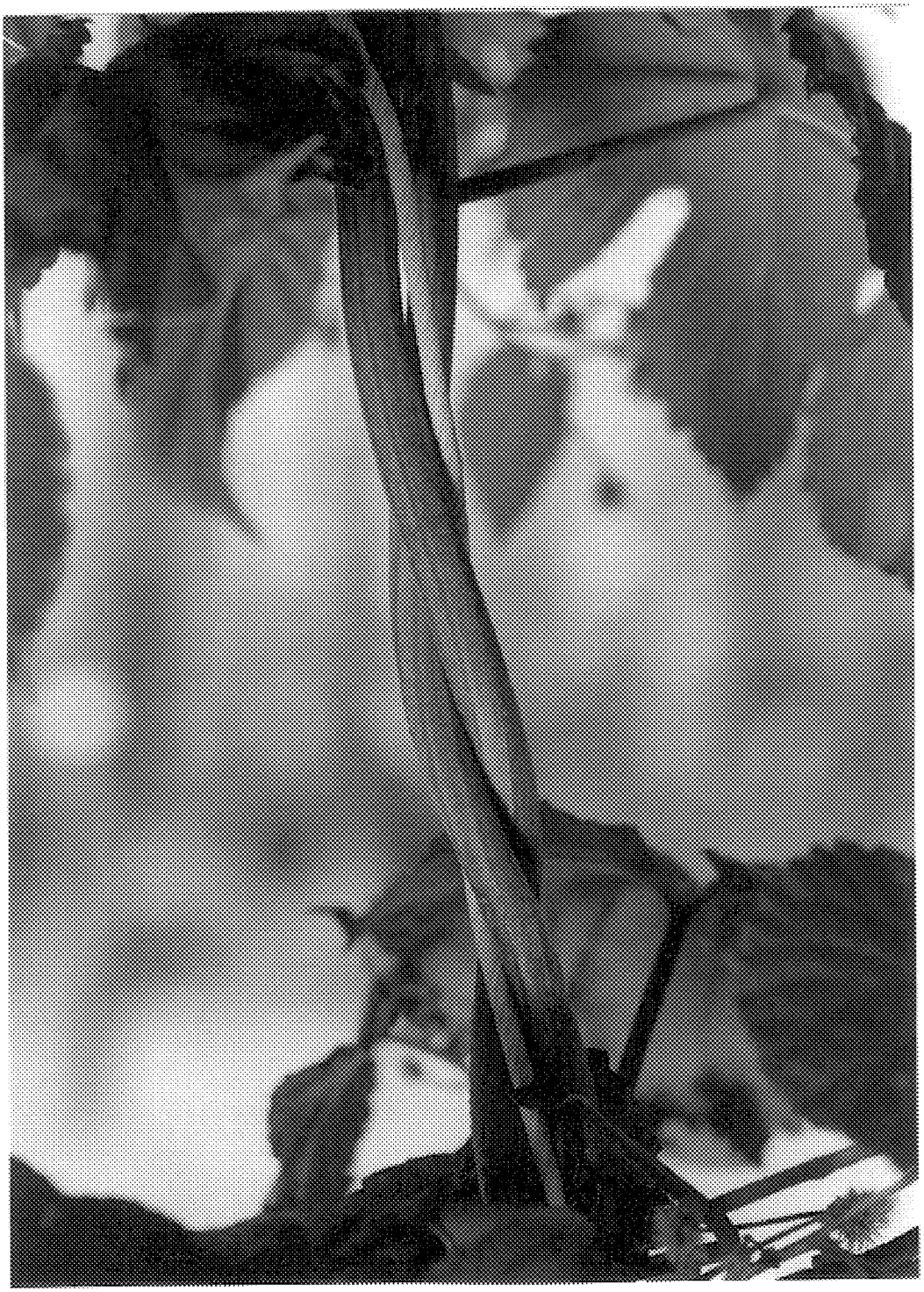
FIG. 5 shows a bine of the new hop plant variety.
Figure 6:
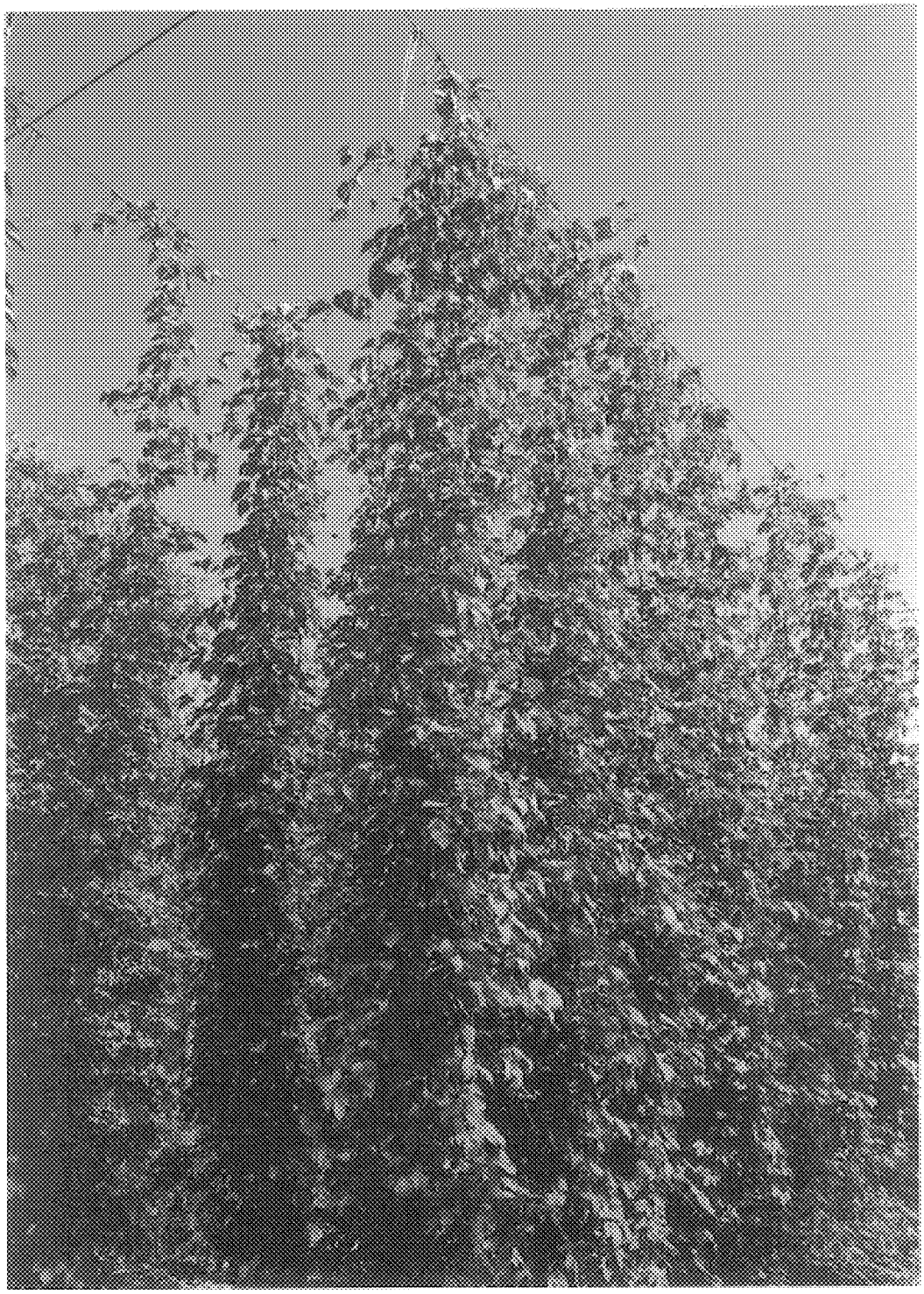
FIG. 6 shows a hop plant of the new variety.

The new hop plant variety is a cultivar of recent origin, used for its bittering and aromatic properties. The new variety is moderately tolerant to powdery mildew and Sphaerotheca. The new variety produces a medium size compact cone with good pickability (similar to Cascade, unpatented) and storageability (25% to 30% alpha loss after 6 months common storage). The cones mature medium early (about September 1 in Granger, Wash., and yield a crop of 2650 to 2880 pounds per acre (2970 to 3230 kg/ha).

The following is a detailed botanical description of the new and distinct variety of *Humulus lupulus*, based on observations of specimens grown in Granger, Wash. during the 1998 growing season. All colors are described according to The Royal Horticultural Society Colour Chart. It should be understood that the botanical and analytical chemical characteristics described will vary somewhat depending upon cultural practices and climate conditions and can vary with location and season.

Bine:
- *Color.*—Yellow green (146C).
- *Stripe.*—Greyed purple (183A).
- *Stipule color.*—Light green.
- *Stipule direction.*—Up, forked.
- *Diameter.*—0.80 cm (measurement taken at 2.75 m).
- *Shoot emergence.*—Medium early to medium; similar to Galena.

Leaves:
- *Leaf arrangement.*—Opposite.
- *Leaf shape.*—Cordate to palmate.
- *Average length.*—17.3 cm.
- *Average width.*—17 cm.
- *Color — upper surface, mature.*—Green (139A).
- *Color — lower surface, mature.*—Green (137B).
- *Color — upper surface, immature.*—Green (137A).
- *Color — lower surface, immature.*—Green (137C).
- *Number of leaf lobes.*—1–5.
- *Margin.*—Serrate.
- *Serrations per inch.*—4 min., 7 max.
- *Pose.*—Downward.
- *Average petiole length.*—8.0 cm.
- *Petiole color at base.*—Greyed purple (183A).
- *Venation.*—Palmate.
- *Vein color.*—Yellow green (146C).

Cones:
- *Average length.*—2.8 cm.
- *Average diameter.*—1.5 cm.
- *Color.*—Bract: Yellow green (144A). Bracteole: Yellow green (145C).
- *Shape.*—Ovoid.
- *Bract shape.*—Ovate.
- *Bract tip shape.*—Acute.
- *Bract tip position.*—Appressed.
- *Bracteole shape.*—Lanceolate.
- *Shattering potential at harvest average for commercial varieties.*—Similar to Cascade.
- *% Alpha acids.*—12.0%–14.0% of cone weigh (ASBC Spectrophotometric method).

*% Beta acids.*—4.0%–5.0% of cone weight (ASBC Spectrophotometric method).

*% Cohumulone.*—15.0%–20.0% of alpha acids.

*Total oils.*—2.0–2.5 mL/100 g.

*Aroma.*—Sharp, floral with spicy notes.

Analytical data: Essential oil profile of YCR Accession No. 14: 110 mg of 10% Adsorbate/150C/5 Min. by DTD-GC-MS.

| MS Spec # | Area Integration | Peak Assignment | Area % |
|---|---|---|---|
| 77–246 | 39360 | acetone + isoprene | 0.484 |
| 306–322 | 7766 | 2-methyl-3-buten-1-ol | 0.096 |
| 336 | 1454 | pentanal ? | 0.018 |
| 352 | 266 | hexene | 0.003 |
| 389 | 850 | formic acid | 0.010 |
| 396 | 6832 | acetic acid | 0.084 |
| 422 | 488 | methylpentanone | 0.006 |
| 430 | 932 | ?m/z 56, 70 peaks | 0.011 |
| 457 | 2767 | 3-methyl-2-butenal | 0.034 |
| 471 | 1795 | hexanal | 0.022 |
| 478 | 3315 | isobutyric acid | 0.041 |
| 489 | 3359 | n-octane | 0.041 |
| 539 | 11204 | 3-methylbutyric acid | 0.138 |
| 545 | 2082 | 2-methylbutyric acid | 0.026 |
| 548 | 972 | 2-methyl-2-butanol acetate | 0.012 |
| 555 | 301 | ? m/z 82/81/67 peaks | 0.004 |
| 561 | 245 | ? m/z 81 peak | 0.003 |
| 565 | 738 | propanoic acid | 0.009 |
| 579 | 26435 | 4-penten-2-ol + 2,6-dimethyl-2,4-heptadiene | 0.325 |
| 592 | 4135 | 5,5-dimethyl-2(5H)-furanone | 0.051 |
| 603 | 980 | alpha-pinene | 0.012 |
| 611 | 128 | propylisobutyrate | 0.002 |
| 617 | 1236 | dimethyltrisulfide | 0.015 |
| 626 | 9978 | 2-methylbutylpropanoate | 0.123 |
| 634 | 235 | 6-methyl-5-heptene-2-one | 0.003 |
| 638 | 15055 | beta-pinene + hexanoic acid | 0.185 |
| 652 | 1521624 | myrcene | 18.728 |
| 655 | 9934 | 2,7-dimethyl-2,6-octadiene | 0.122 |
| 663 | 26663 | isobutyl-2-methylbutyrate | 0.328 |
| 667 | 31112 | 3-methylbutylisobutyrate | 0.383 |
| 671 | 19675 | methylheptanoate | 0.242 |
| 674 | 200 | alpha-terpinene | 0.002 |
| 677 | 418 | p-cymene | 0.005 |
| 685 | 10340 | limonene + beta-phellandrene | 0.127 |
| 690 | 244 | ? terpene | 0.003 |
| 698 | 4618 | beta-oclmene + pentyl-2-methylpropanoate | 0.057 |
| 712 | 584 | gamma-terpinene | 0.007 |
| 717 | 1726 | Isooctanol | 0.021 |
| 728 | 8437 | heptanoic acid | 0.104 |
| 733 | 31157 | methyl-6-methylheptanoate + 2-nonanone | 0.383 |
| 738 | 1362 | linalool oxide | 0.017 |
| 747 | 34668 | linalool + nonanal + 3-(4-methyl-3-pentenyl)-furan | 0.427 |
| 752 | 8440 | 2-methylbutyl-2-methylbutyrate | 0.104 |
| 756 | 9488 | pentyl-3-methylbutyrate | 0.117 |
| 762 | 292 | ? terpene | 0.004 |
| 769 | 34847 | methyloctanoate | 0.429 |
| 775 | 1026 | | 0.013 |
| 779 | 3860 | 2,3-dihydro-3,5-dihydroxy-6-methyl-4(H)-pyran-4-one | 0.048 |
| 790 | 5801 | octanoic acid (branched isomer) | 0.071 |
| 797 | 1219 | hexylisobutyrate | 0.015 |
| 800 | 312 | cis-3-hexenylisobutyrate | 0.004 |
| 802 | 614 | 2-decanone (branched isomer) | 0.006 |
| 806 | 220 | 2-decanone (branched isomer) | 0.003 |
| 815 | 492 | ? terpene m/z 41/69 peaks | 0.006 |
| 829 | 27744 | ? 130 m.w.branched alcohol m/z 59 base peak + octanoic acid | 0.341 |
| 836 | 1313 | ? terpene m/z 41/69/152 peaks | 0.016 |
| 841 | 13019 | 2-decanone | 0.160 |
| 846 | 6935 | methyl-4-octenoate | 0.065 |
| 852 | 241 | | 0.003 |

-continued

| MS Spec # | Area Integration | Peak Assignment | Area % |
|---|---|---|---|
| 858 | 1223 | heptylpropanoate | 0.015 |
| 864 | 4438 | methylnonenoate | 0.055 |
| 881 | 24061 | methylnonanoate | 0.296 |
| 886 | 2321 | nerol | 0.029 |
| 892 | 460 | | 0.006 |
| 899 | 235 | | 0.003 |
| 904 | 531 | | 0.007 |
| 910 | 2019 | 2-methylheptylpropanoate | 0.025 |
| 915 | 66621 | geraniol | 0.820 |
| 918 | 18565 | 2-undecanone (branched isomer) | 0.228 |
| 925 | 1264 | ? terpene m/z 41/69 peaks | 0.016 |
| 939 | 20854 | undecenyl alcohol | 0.257 |
| 950 | 1126 | octenyl acetate | 0.014 |
| 955 | 166 | ? 180 m.w., 95 base peak, possibly bornylformate | 0.002 |
| 963 | 101264 | methyldecanoate (branched isomer) + 2-undecanone | 1.246 |
| 978 | 920 | octylpropanoate | 0.011 |
| 963 | 160309 | methyl-4-decenoate + methyl-4,8-decadienoate | 1.973 |
| 996 | 51491 | methylgeranate | 0.634 |
| 1004 | 40310 | methyldecanoate | 0.496 |
| 1016 | 1736 | decanoic acid (branched isomer) | 0.021 |
| 1034 | 6140 | octyl-2-methylpropanoate | 0.076 |
| 1039 | 958 | ? unsaturated alcohol or aldehyde | 0.012 |
| 1050 | 14056 | 2-dodecanone (branched isomer) | 0.173 |
| 1057 | 6412 | alpha-cubebene | 0.079 |
| 1064 | 6428 | decanoic acid | 0.079 |
| 1073 | 3240 | geranyl acetate | 0.040 |
| 1078 | 1933 | ? acetate | 0.024 |
| 1082 | 23 | possibly bornylacetate | 0.000 |
| 1087 | 6203 | alpha-ylangene + methylundecanoate (branched isomer) | 0.076 |
| 1092 | 29196 | alpha-copaene + 2-dodecanone | 0.359 |
| 1107 | 2850 | ? 204 m.w. sesquiterpene | 0.035 |
| 1113 | 3500 | methylundecadienoate | 0.043 |
| 1123 | 1495 | methyl -10-undecenoate | 0.018 |
| 1129 | 1024 | ? sesquiterpene 206 m.w. 163 base peak | 0.013 |
| 1135 | 2161 | methylundecanoate | 0.027 |
| 1151 | 1612921 | caryophyllene | 19.852 |
| 1159 | 33311 | beta-cubebene | 0.410 |
| 1164 | 835 | | 0.010 |
| 1169 | 1805 | ? sesquiterpene 206 m.w. 163 base peak | 0.022 |
| 1180 | 5290 | 2-tridecanone (branched isomer) | 0.065 |
| 1196 | 3160413 | humulene | 38.898 |
| 1200 | 2148 | ? 204 m.w. sesquiterpene 161 base peak | 0.026 |
| 1204 | 350 | methyldodecenoate | 0.004 |
| 1215 | 67631 | gamma-muurolene | 0.832 |
| 1224 | 45481 | 2-tridecanone | 0.560 |
| 1230 | 24862 | metyldodecenoate (branched isomer) | 0.306 |
| 1238 | 176494 | methyl-3,6-decadienoate | 2.172 |
| 1246 | 53191 | geranyl isobutyrate + alpha-selinene (scan 1242) | 0.655 |
| 1251 | 20079 | methyldodecenoate + delta-cadinene | 0.247 |
| 1262 | 64843 | alpha-muurolene | 0.798 |
| 1266 | 2064 | calamenene | 0.025 |
| 1273 | 95640 | beta-cardinene | 1.177 |
| 1276 | 1865 | delta-selinene | 0.023 |
| 1285 | 10335 | sesquiterpene w/no common name CAS#16728-99-7, cadinene-type | 0.127 |
| 1292 | 11255 | ? sesquiterpene 200 m.w. 157 base peak | 0.139 |
| 1308 | 10505 | dodecatrienoic acid | 0.129 |
| 1318 | 12734 | tetradecadienol | 0.157 |
| 1332 | 1349 | caryophyllyl alcohol | 0.017 |
| 1342 | 19979 | caryophyllene oxide | 0.246 |
| 1348 | 2006 | methyltridecadienoate | 0.025 |
| 1356 | 12300 | 2-tetradecanone + methyl-tridecenoate + humulene epoxide | 0.151 |
| 1367 | 2300 | methyltridecenoate | 0.028 |
| 1373 | 34158 | humulene epoxide | 0.420 |
| 1379 | 247 | | 0.003 |

-continued

| MS Spec # | Area Integration | Peak Assignment | Area % |
|---|---|---|---|
| 1384 | 2559 | ? sesquiterpene m/z 204/179 | 0.031 |
| 1390 | 231 | ? 222 m.w. sesquiterpene | 0.003 |
| 1399 | 11574 | globutol | 0.142 |
| 1411 | 15578 | delta-cadinol | 0.192 |
| 1429 | 35634 | pentadecatrienol | 0.439 |
| 1436 | 821 | 2-pentadecanone (branched isomer) | 0.010 |
| 1445 | 12234 | pentadecadienol | 0.151 |
| 1451 | 5168 | heptadecatriene | 0.064 |
| 1463 | 770 | heptadecatriene | 0.009 |
| 1467 | 1248 | heptadecatriene | 0.015 |
| 1481 | 1416 | 2-pentadecanone | 0.017 |
| 1499 | 968 | caryophyllyl acetate | 0.012 |

-continued

| MS Spec # | Area Integration | Peak Assignment | Area % |
|---|---|---|---|
| 1580 | 2392 | ? 250 m.w. w/115 base peak | 0.029 |
| 1772 | 703 | ? long chain isoprenoid compound | 0.009 |
| 1944–1995 | 337102 | mix of hop acid analogues (lupulon, humulon + dihydro derivatives) | |
| | 8124778 | Total Essential Oil Components (minus hop acids) | 100.000 |

I claim:

1. A new variety of hop plant, substantially as herein shown and described.

* * * * *